US00PP28936P2

(12) United States Plant Patent
Jackson et al.

(10) Patent No.: US PP28,936 P2
(45) Date of Patent: Feb. 6, 2018

(54) ***CORNUS* PLANT NAMED 'JN6'**

(50) Latin Name: *Cornus kousa*
Varietal Denomination: JN6

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

( * ) Notice: Subject to any disclaimer, the term of this patent is extended or adjusted under 35 U.S.C. 154(b) by 0 days.

(21) Appl. No.: 15/330,537

(22) Filed: Oct. 5, 2016

(51) Int. Cl.
*A01H 5/00* (2006.01)

(52) U.S. Cl.
USPC ..... Plt./220

(58) Field of Classification Search
USPC ..... Plt./220
See application file for complete search history.

*Primary Examiner* — Annette H Para
(74) *Attorney, Agent, or Firm* — Penny J. Aguirre

(57) ABSTRACT

A new cultivar of *Cornus kousa* plant named, 'JN6', that is characterized by its foliage that is dark green with a bluish cast in color and a glossy sheen, its leaves that are large in size, and its vigorous growth habit.

2 Drawing Sheets

Botanical classification: *Cornus kousa.*
Variety denomination: 'JN6'.

BACKGROUND OF THE INVENTION

The present invention relates to a new and distinct cultivar of *Cornus kousa*, and will be referred to hereafter by its cultivar name, 'JN6'. 'JN6' is a new cultivar of dogwood, a shrub grown for use as an ornamental landscape plant.

The Inventors discovered the new cultivar as a chance seedling growing in a field at his nursery in Belvidere, Tenn. in May of 2011. The field had been planted with seeds collected from an unnamed and unpatented plants of *Cornus kousa.*

Asexual propagation of the new cultivar was first accomplished by one of the Inventors using chip budding in summer of 2011 in Belvidere, Tenn. Asexual propagation of the new cultivar by chip budding has been determined that the characteristics are stable and are reproduced true to type in successive generations.

SUMMARY OF THE INVENTION

The following traits have been repeatedly observed and represent the characteristics of the new cultivar as grown outdoors in a trial plot in Perry, Ohio. These attributes in combination distinguish 'JN6' as unique cultivar of *Cornus.*

1. 'JN6' exhibits foliage that is dark green with a bluish cast in color and a glossy sheen.
2. 'JN6' exhibits leaves that are large in size.
3. 'JN6' exhibits a vigorous growth habit; greater than typical for *Cornus kousa* and cultivars of *Cornus kousa* known to the Inventors.

'JN6' can be most closely compared to the cultivars of *Cornus kousa*, 'Avalanche' (not patented) and 'Greensleeves' (not patented). Both cultivars are similar to 'JN6' in having flowers of similar size and color, in flowering time, and in branch habit. Both cultivars differ from 'JN6' in having foliage that is lighter green in color, in having foliage that is dull in texture, in having a less vigorous growth habit in production, and in having foliage that is smaller in length and width.

BRIEF DESCRIPTION OF THE DRAWINGS

The accompanying colored photographs illustrate the overall appearance and distinct characteristics of the new *Cornus*. The photographs were taken of a two year-old plant as grown outdoors in a trial plot in Perry, Ohio.

The photograph in FIG. 1 provides a side view of the plant habit of 'JN6'.

Figure 1:
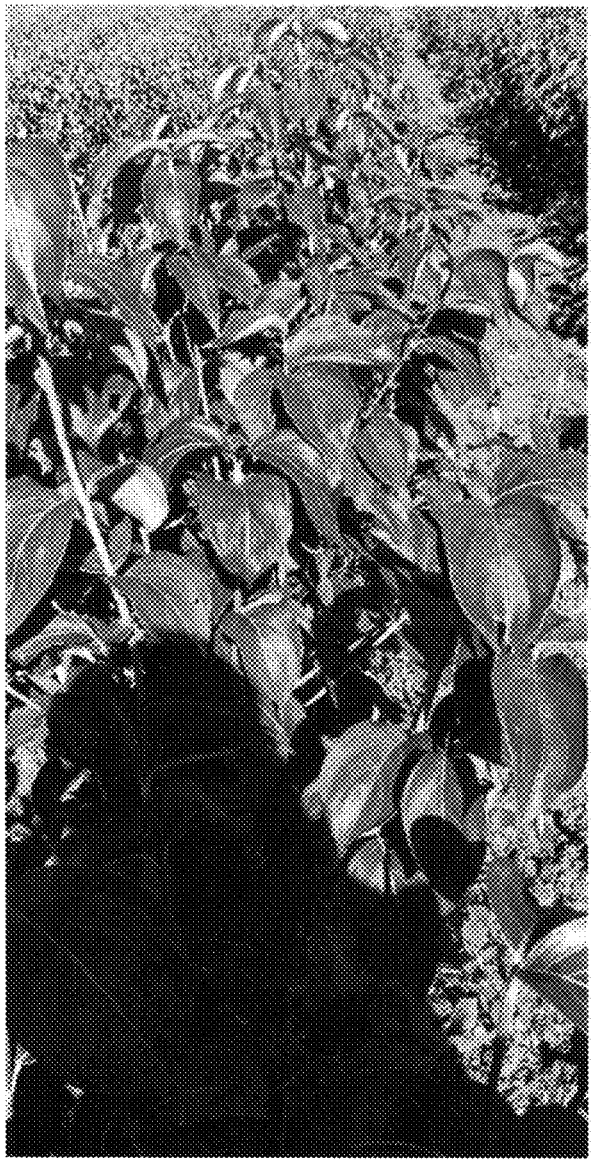
Figure 2:
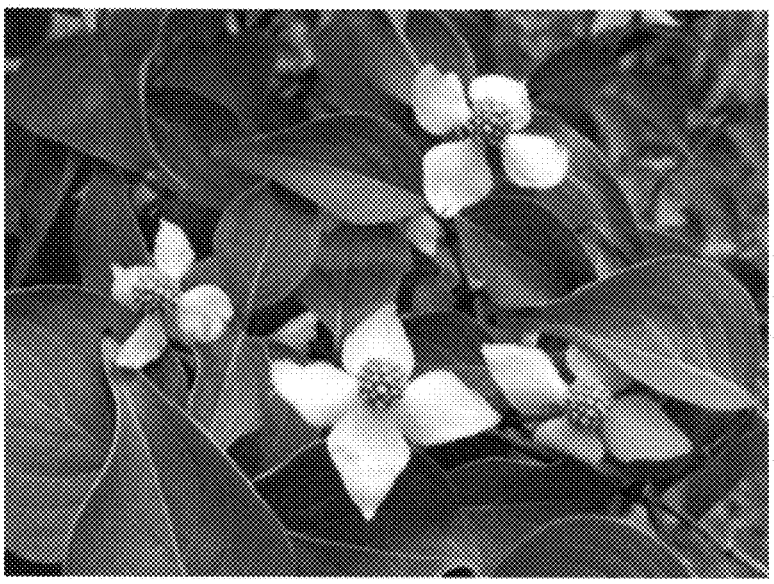

The photograph in FIG. 2 provides a view of the flowers of 'JN6'.

Figure 3:
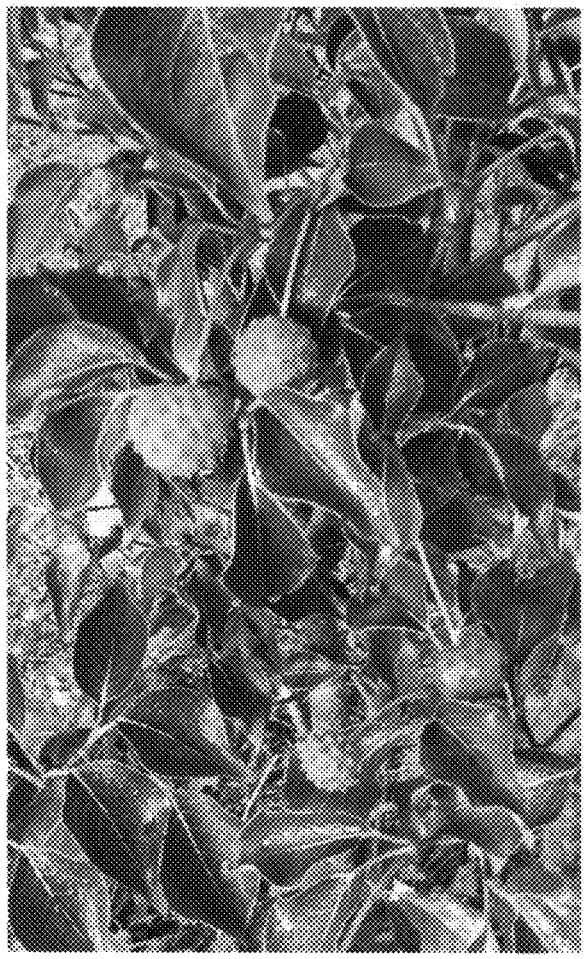

The photograph in FIG. 3 provides a view of the fruit of 'JN6'.

The colors in the photographs are as close as possible with the photographic and printing technology utilized and the color values cited in the detailed botanical description accurately describe the colors of the new *Cornus.*

DETAILED BOTANICAL DESCRIPTION

The following is a detailed description of two year-old plants the new *Cornus* as grown in 10-gallon containers in Perry, Ohio. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Blooms for three weeks in mid-summer in in Northeastern Ohio.

*Plant type.*—Deciduous shrub.

*Plant habit.*—Upright, vase-shaped with a rounded top.

*Plant height and spread.*—Reaches up to 9.14 m in height and spread as a mature tree in the landscape and 1.2 m in height and 60 cm in spread in a 10-gallon container.

*Diseases and pests*.—No susceptibility and resistance to diseases or pests has been observed.

*Cold hardiness*.—At least in U.S.D.A. Zones 5 to 8.

*Root description*.—Fibrous and fine.

*Propagation*.—Chip budding.

*Time to develop a young plant*.—1 year.

*Growth rate*.—Moderate but vigorous for *Cornus Kousa*.

Branch description:

*Branch shape*.—New growth; squared to rounded, mature branches; rounded.

*Branch color*.—New growth; 139C suffused with 63B at the base, maturing wood; N200 overlaid with 177B, bark N200B.

*Branch size*.—Main branches; an average of 0.9 m in length and 10 cm in width measured 60 cm above the soil level, lateral branches; up to 40 cm in length and 5 mm in width.

*Branch surface*.—New growth; smooth, dull, and lightly pubescent with very small hairs NN155D in color, mature stems and bark; glabrous and heavily covered with lenticels an less than about 0.5 mm in length and 199D in color.

*Internode length*.—An average of 13 cm in length.

*Branching*.—An average of 1 to 3 basal branches with an average of 8 lateral branches, per basal branch.

Foliage description:

*Leaf shape*.—New leaves; lanceolate, mature leaves; oval to elliptic.

*Leaf division*.—Simple.

*Leaf base*.—Cuneate to oblique.

*Leaf apex*.—Acuminate.

*Leaf fragrance*.—None.

*Leaf venation*.—Pinnate, color; upper surface 145A to 145B and lower surface; 145C to 145D.

*Leaf margins*.—Entire and undulate.

*Leaf arrangement*.—Opposite.

*Leaf attachment*.—Petiolate.

*Leaf surface*.—New leaves upper and lower surface; smooth and very slightly puberulent, glossy sheen, mature leaf upper surface; smooth and very slightly puberulent with a satiny sheen.

*Leaf color*.—Newly expanded leaves upper surface; 137B and lower surface; 147B, mature leaves upper surface; a color between 139A and 136A and lower surface; a color between 147B and 147C.

*Petioles*.—An average of 2 cm in length and 2 mm in width, 145A in color, smooth surface is very slightly pubescent with very small hairs NN155D in color.

*Stipules*.—Occasional, lanceolate in shape, an average of 3 mm in length and 2 mm in width, acute apex, truncate base, 145B in color.

Inflorescence description:

*Inflorescence type*.—Round bracteolate umbel.

*Inflorescence size*.—An average of 1 cm in length and 1.4 cm in diameter.

*Flower buds*.—Oblong in shape, 143C in color, an average of 2.5 mm in length and 1.25 mm in width.

*Flower fragrance*.—None.

*Lastingness of inflorescence*.—3 weeks in mid-summer.

*Flower quantity*.—An average of 59 flowers per inflorescence.

*Flower type*.—Rotate.

*Flower size*.—An average of 5 mm in diameter and 1 mm in depth.

*Peduncles*.—Primary an average of 10 cm in length to base of inflorescence and 2 mm in diameter with secondary an average of 12 cm in length and 2 mm in width and tertiary an average of 10.5 mm in length and 2 mm in width, 145A in color, glabrous and dull surface, round in shape, strong.

*Pedicels*.—None present.

*Bracts*.—4, obovate in color, acuminate apex, truncate base, 161D in color, spreading, glabrous on both surfaces, an average of 5.3 cm in length and 2.9 cm in width.

*Sepals*.—4, fused, 143C in color, acute apex, 1.5 mm in length and 1 mm in width, glabrous and dull surface.

*Petals*.—4, base fused to top of calyx, spreading, oblong in shape, 2 mm in length and 1 mm in width, margins entire, apex acute, outer and inner surface is glabrous, color of inner and outer surface is 145C.

Reproductive organs:

*Gynoecium*.—1 pistil, style is about 1.5 mm in length, and 143C in color, stigma is about 0.5 mm in diameter, globose in shape and 145D in color, ovary is disked shape, about 1.5 mm in diameter and 143C in color.

*Androcoecium*.—4 stamens, about 2.5 mm in length, all exserted beyond corolla, filaments are translucent and 155A in color and about 2 mm in length, anthers are about 0.5 mm in length, 199C in color, pollen is moderate in quantity and 8D in color.

*Fruit and seed*.—True berry, globose in shape, surface knobby and matte when mature, about 22 mm in diameter, present in late summer, matures to N34B in color, seed; 6, oblong in shape, 9 mm in length and 5 mm in width in size and 166C in color.

It is claimed:

1. A new and distinct cultivar of *Cornus* plant named 'JN6' as herein illustrated and described.

* * * * *